United States Patent [19]
Porter et al.

[11] Patent Number: 5,530,128
[45] Date of Patent: Jun. 25, 1996

[54] N-SULPHONYLAMINO DERIVATIVES OF DIPETIDE COMPOUNDS AS METALLOPROTEINASE INHIBITORS

[75] Inventors: John R. Porter; John R. Morphy; Thomas A. Millican, all of Berkshire; Nigel R. A. Beeley, Oxfordshire, all of United Kingdom

[73] Assignee: Celltech Therapeutics Limited, Berkshire, United Kingdom

[21] Appl. No.: 182,160

[22] PCT Filed: Jun. 3, 1993

[86] PCT No.: PCT/GB93/01185

§ 371 Date: Feb. 2, 1994

§ 102(e) Date: Feb. 2, 1994

[87] PCT Pub. No.: WO93/24475

PCT Pub. Date: Dec. 9, 1993

[30] Foreign Application Priority Data

Jun. 3, 1992 [GB] United Kingdom ............... 9211707

[51] Int. Cl.$^6$ .................. C07D 295/22; C07D 307/06; A61K 31/095; A61K 31/535
[52] U.S. Cl. .............. 544/159; 544/160; 560/12; 560/13; 560/14; 560/312; 560/79
[58] Field of Search ................ 544/159, 160; 560/12, 13, 14, 312; 514/238.2, 507, 600; 564/79

[56] References Cited

U.S. PATENT DOCUMENTS

| | | | |
|---|---|---|---|
| 4,791,102 | 12/1988 | Bernat et al. | 514/19 |
| 4,814,342 | 3/1989 | Hoover et al. | 514/385 |
| 4,918,105 | 4/1990 | Cartwright et al. | 514/575 |
| 4,937,243 | 6/1990 | Markwell et al. | 514/237.8 |
| 4,996,358 | 2/1991 | Handa et al. | 562/621 |
| 5,037,087 | 8/1991 | Patchett et al. | 514/19 |
| 5,122,523 | 6/1992 | Morishima et al. | 514/227.5 |
| 5,126,451 | 6/1992 | Kaltenbron et al. | 544/159 |
| 5,162,527 | 11/1992 | Doherty et al. | 544/159 |
| 5,180,735 | 1/1993 | Kishimoto et al. | 514/443 |
| 5,194,608 | 3/1993 | Toyoda | 544/122 |
| 5,256,657 | 10/1993 | Singh et al. | 514/228.2 |
| 5,260,278 | 11/1993 | Himmelsbach et al. | 514/19 |
| 5,275,950 | 1/1994 | Dickman et al. | 435/280 |
| 5,284,849 | 2/1994 | Rosenberg et al. | 514/252 |
| 5,300,501 | 4/1994 | Porter et al. | 514/238.2 |
| 5,304,604 | 4/1994 | Davidson et al. | 514/238.2 |

FOREIGN PATENT DOCUMENTS

| | | | |
|---|---|---|---|
| 0214639 | 3/1987 | European Pat. Off. | 562/621 |
| 0231081 | 8/1987 | European Pat. Off. | 562/621 |
| 0236872 | 9/1987 | European Pat. Off. | 562/621 |
| 0274453 | 7/1988 | European Pat. Off. | 574/575 |
| 0489577 | 6/1992 | European Pat. Off. | 562/621 |
| 90/05716 | 5/1990 | WIPO | 514/575 |
| 90/05719 | 5/1990 | WIPO | 562/621 |
| 91/15507 | 10/1991 | WIPO | 562/621 |
| 93/24475 | 12/1993 | WIPO | 544/159 |

OTHER PUBLICATIONS

Wahl, et al., "Biochemistry and Inhibition of Collagenase and Stromelysin" Chapter 19, Annual Reports in Medicinal Chemistry, 1989, pp. 177–184.

*Primary Examiner*—Floyd D. Higel
*Attorney, Agent, or Firm*—Foley & Lardner

[57] ABSTRACT

Compounds of formula (1) are described wherein R represents a —CONHOH, carboxyl, carboxyl ester, or —P(O)($X^1R^8$)$X^2R^9$, where $X^1$ and $X^2$ are the same or different and each is oxygen or sulphur, $R^8$ and $R^9$ are the same or different and each represents hydrogen or an optionally substituted alkyl, aryl or aralkylthioalkyl group; $R^2$ represents an optionally substituted alkyl, alkenyl, cycloalkyl, cycloalkylalkyl, aryl, aralkyl, aralkoxy, or aralkylthio group, or an amino, substituted amino, carboxyl, or carboxyl ester group; $R^3$ represents hydrogen or alkyl; $R^4$ represents hydrogen or alkyl; $R^5$ represents an optionally substituted alkyl or alkenyl group optionally interrupted by one or more —O— or —S— atoms or —N($R^7$)— groups, where $R^7$ is a hydrogen atom or a $C_{1-6}$ alkyl group, or —(Alk)$_n R^6$ where Alk is an alkyl or alkenyl group optionally interrupted by one or more —O— or —S— atoms or —N($R^7$)— groups, n is zero or 1, and $R^6$ is an optionally substituted cycloalkyl or cycloalkenyl group; X represents —NR$^{10}$R$^{11}$ where $R^{10}$ is hydrogen or an optionally substituted alkyl, alkanoyl, aryl, aroyl, aralkyl or aralkanoyl group, and $R^{11}$ is a straight or branched alkylaminosulphonylamino group wherein the alkyl portion is optionally interrupted by one or more —O— or —S— atoms of —N($R^7$)— or aminocarbonyloxy groups; or the salts, solvates and hydrates thereof. The compounds are metalloproteinase inhibitors and in particular have a selective inhibitory action against gelatinase and are useful in the treatment of cancer to control tumor metastasis.

10 Claims, No Drawings

N-SULPHONYLAMINO DERIVATIVES OF DIPETIDE COMPOUNDS AS METALLOPROTEINASE INHIBITORS

FIELD OF THE INVENTION

This invention relates to a novel class of peptidyl derivatives, to processes for their preparation and to their use in medicine.

BACKGROUND OF THE INVENTION

In normal tissues, cellular connective tissue synthesis is offset by extracellular matrix degradation, the two opposing effects existing in dynamic equilibrium. Degradation of the matrix is brought about by the action of proteinases released from resident connective tissue cells and invading inflammatory cells, and is due, in part, to the activity of at least three groups of metalloproteinases. These are the collagenases, the gelatinases (or type-IV collagenases) and the stromelysins. Normally these catabolic enzymes are tightly regulated at the level of their synthesis and secretion and also at the level of their extracellular activity, the latter through the action of specific inhibitors, such as α2-macroglobulins and TIMP (tissue inhibitor of metalloproteinase), which form inactive complexes with metalloproteinases.

The accelerated, uncontrolled breakdown of connective tissues by metalloproteinase catalysed resorption of the extracellular matrix is a feature of many pathological conditions, such as rheumatoid arthritis, corneal, epidermal or gastric ulceration; tumour metastasis or invasion; periodontal disease and bone disease. It can be expected that the pathogenesis of such diseases is likely to be modified in a beneficial manner by the administration of metalloproteinase inhibitors and numerous compounds have been suggested for this purpose [for a general review see Wahl, R. C. et al Ann. Rep. Med. Chem. 25, 175–184, Academic Press Inc., San Diego (1990)].

Certain hydroxamic acid peptidyl derivatives [see for example European Patent Specifications Nos. 214639, 231081, 236872 and 274453 and International Patent Specifications Nos. WO90/05716 and WO90/05719], have been described as collagenase and/or stromelysin inhibitors.

SUMMARY OF THE INVENTION

We have a now found a new class of peptidyl derivatives, members of which are metalloproteinase inhibitors and which, in particular, advantageously possess a potent and selective inhibitory action against gelatinase.

There is now much evidence that metalloproteinases are important in tumour invasion and metastasis. Tumour cell gelatinase, in particular, has been associated with the potential of tumour cells to invade and metastasise. Tumour invasion and metastasis is the major cause of treatment failure for cancer patients, and the use of a selective gelatinase inhibitor such as a compound of the present invention which is capable of inhibiting tumour cell invasion can be expected to improve the treatment of this disease.

Thus according to one aspect of the invention we provide a compound of formula (1)

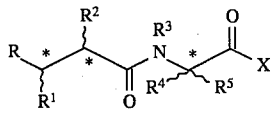

(1)

wherein R represents a —CONHOH, carboxyl (—CO$_2$H), esterified carboxyl or —P(O)(X$^1$R$^8$)X$^2$R$^9$ group, where X$^1$ and X$^2$, which may be the same or different is each an oxygen or a sulphur atom, and R$^8$ and R$^9$, which may be the same or different each represents a hydrogen atom or an optionally substituted alkyl, aryl, or aralkyl group.

R$^1$ represents a hydrogen atom or an optionally substituted alkyl, alkenyl, aryl, aralkyl, heteroaralkyl or heteroarylthioalkyl group;

R$^2$ represents an optionally substituted alkyl, alkenyl, cycloalkyl, cycloalkylalkyl, aryl, aralkyl, aralkoxy, or aralkylthio group, or an amino (—NH$_2$), substituted amino, carboxyl (—CO$_2$H) or esterified carboxyl group;

R$^3$ represents a hydrogen atom or an alkyl group;

R$^4$ represents a hydrogen atom or an alkyl group;

R$^5$ represents an optionally substituted alkyl or alkenyl group optionally interrupted by one or more —O— or —S— atoms or —N(R$^7$)— groups, [where R$^7$ is a hydrogen atom or a C$_{1-6}$alkyl group] or a group —[Alk]$_n$R$^6$ where Alk is an alkyl or alkenyl group optionally interrupted by one or more —O— or —S— atoms or —N(R$^7$)— groups, n is zero or an integer 1, and R$^6$ is an optionally substituted cycloalkyl or cycloalkenyl group;

X represents a group —NR$^{10}$R$^{11}$ where R$^{10}$ is a hydrogen atom or an optionally substituted alkyl, alkanoyl, anyl, aroyl, aralkyl or aralkanoyl group, and R$^{11}$ is a straight or branched alkylaminosulphonylamino group wherein the alkyl portion is optionally interrupted by one or more —O— or —S— atoms or —N(R$^7$)— or aminocarbonyloxy groups;

and the salts, solvates and hydrates thereof.

It will be appreciated that the compounds according to the invention can contain one or more asymmetrically substituted carbon atoms, for example those marked with an asterisk in formula (1). The presence of one or more of these aysmmetric centres in a compound of formula (1) can give rise to stereoisomers, and in each case the invention is to be understood to extend to all such stereoisomers, including enantiomers and diastereoisomers, and mixtures, including racemic mixtures, thereof.

In the formulae herein, the ∼ line is used at a potential asymmetric centre to represent the possibility of R- and S-configurations, the ━━ line and the ── line to represent an unique configuration at an asymmetric centre.

In the compounds according to the invention, when the group R represents an esterified carboxyl group, it may be for example a group of formula —CO$_2$R$^{18}$ where R$^{18}$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$alkyl group such as an optionally substituted phenyloxymethyl, phenyloxyethyl, 1-naphthyloxymethyl or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the groups R$^{18}$ include for example one or more halogen atoms such as fluorine, chlorine, bromine or iodine atoms, or C$_{1-4}$alkyl, e.g. methyl or ethyl, or C$_{1-4}$alkoxy, e.g. methoxy or ethoxy, groups.

In general, when the group R represents an esterified carboxyl group, it may be a metabolically labile ester of a carboxylic acid.

When the groups $R^1$ and/or $R^2$ in compounds of formula (1) each represents an optionally substituted alkyl or alkenyl group, it may be, for example, a straight or branched $C_{1-6}$ alkyl or $C_{2-6}$alkenyl group, such as a methyl, ethyl, n-propyl, i-propyl, n-butyl, i-butyl, s-butyl, t-butyl, n-pentyl, i-penty, n-hexyl, ethenyl, 1-propenyl, 1-butenyl or 2-butenyl group optionally substituted by one or more $C_{1-6}$alkoxy, e.g. methoxy, ethoxy, propoxy, $C_{1-6}$alkylthio, e.g. methylthio, ethylthio, propylthio, $C_{6-12}$aryl$C_{1-6}$alkoxy, e.g. phenyl$C_{1-6}$ alkoxy such as benzyloxy, aralkylthio, e.g phenyl$C_{1-6}$alkylthio such as benzylthio, amino (—NH$_2$), substituted amino, [such as —NHR$^{19}$, where $R^{19}$ is a $C_{1-6}$ alkyl e.g. methyl or ethyl, $C_{6-12}$aryl$C_{1-6}$alkyl, e.g. phenyl$C_{1-6}$alkyl, such as benzyl, $C_{6-12}$aryl, e.g. phenyl, $C_{3-8}$cycloalkyl, e.g. cyclohexyl, or $C_{3-8}$cycloalkyl$C_{1-6}$alkyl, e.g. cyclohexylmethyl group], carboxyl (—CO$_2$H) or —CO$_2$R$^{18}$ [where $R^{18}$ is as defined above] groups.

Aryl groups represented by $R^1$ and/or $R^2$ in compounds of formula (1) include $C_{6-12}$ aryl groups such as phenyl or 1- or 2-naphthyl groups.

Aralkyl groups represented by $R^1$ and/or $R^2$ include $C_{6-12}$aryl$C_{1-6}$alkyl groups such as phenyl$C_{1-6}$alkyl, or 1-or 2-naphthyl$C_{1-6}$alkyl, for example benzyl, phenylethyl, phenylpropyl, phenylbutyl, phenylpentyl, 1- or 2-naphthylmethyl, naphthylethyl, naphthylpropyl, naphthylbutyl or naphthylpentyl groups.

When the group $R^1$ in compounds of formula (1) is a heteroaralkyl group, it may be for example a $C_{3-6}$heteroaryl$C_{1-6}$alkyl group, such as an optionally substituted pyrrolylmethyl, furanylmethyl, thienylmethyl, imidazolylmethyl, oxazolylmethyl, thiazolylmethyl, pyrazolylmethyl, pyridinylmethyl or pyrimidinylmethyl group.

Heteroarylthioalkyl groups represented by $R^1$ include $C_{3-6}$heteroarylthio$C_{1-6}$alkyl groups such as optionally substituted pyrrolylthiomethyl, furanylthiomethyl, oxazolylthiomethyl, thiazolylthiomethyl, pyrazolylthiomethyl, pyridinylthiomethyl or pyrimidinylthiomethyl groups.

Optional substituents which may be present on heteroaralkyl or heteroarylthioalkyl groups represented by $R^1$ include those discussed below in relation to $R^1$ and/or $R^2$ when these groups are for example aralkyl or aralkylthioalkyl groups.

Cycloalkyl groups represented by the group $R^2$ in compounds according to the invention include $C_{3-8}$cycloalkyl groups such as cyclopentyl or cyclohexyl groups.

When $R^2$ is a cycloalkylalkyl group it may be for example a $C_{3-8}$cycloalkyl$C_{1-6}$alkyl group such as a cyclopentyl$C_{1-6}$alkyl or cyclohexyl$C_{1-6}$alkyl group, for example a cyclopentylmethyl, cyclopentylethyl, cyclopentylpropyl, cyclopentylbutyl, cyclohexylmethyl, cyclohexylethyl, cyclohexylpropyl, or cyclohexylbutyl group.

When $R^2$ is an aralkoxy or an aralkylthio group it may be for example a $C_{6-12}$aryl$C_{1-6}$alkoxy or $C_{6-12}$aryl$C_{1-6}$alkylthio group such as a phenyl$C_{1-6}$alkoxy or phenyl$C_{1-6}$alkylthio group, e.g. a benzyloxy, phenylethoxy, phenylpropoxy, phenylbutoxy, benzylthio, phenylethylthio, phenylpropylthio or phenylbutylthio group.

The cycloalkyl, cycloalkylalkyl, aryl, aralkyl, aralkoxy or aralkylthio groups represented by $R^1$ and/or $R^2$ in compounds of formula (1) may each optionally be substituted in the cyclic part of the group by one, two or more substituents [$R^{16}$] selected from halogen atoms, e.g. fluorine, chlorine, bromine or iodine atoms, or $C_{1-6}$alkyl, e.g. methyl or ethyl, $C_{1-6}$alkoxy e.g. methoxy or ethoxy, $C_{2-6}$alkylenedioxy, e.g. ethylenedioxy, halo$C_{1-6}$alkyl, e.g. tri-fluoromethyl, $C_{1-6}$alkylamino, e.g. methylamino or ethylamino, $C_{1-6}$dialkylamino, e.g. dimethylamino or diethylamino, amino (—NH$_2$), nitro, cyano, hydroxyl (—OH), carboxyl (—CO$_2$H), —CO$_2$R$^{18}$, where $R^{18}$ is as defined above, $C_{1-6}$alkylcarbonyl, e.g. acetyl, sulphonyl (—SO$_3$H) $C_{1-6}$alkylsulphonyl, e.g. methylsulphonyl, aminosulphonyl (—SO$_2$NH$_2$), $C_{1-6}$ alkylaminosulphonyl, e.g. methylaminosulphonyl or ethylaminosulphonyl, $C_{1-6}$dialkylaminosulphonyl e.g. dimethylaminosulphonyl or diethylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino (—NHSO$_2$H), $C_{1-6}$alkylsulphonylamino, e.g. methylsulphonylamino or ethylsulphonylamino, or $C_{1-6}$dialkylsulphonylamino, e.g. dimethylsulphonylamino or diethylsulphonylamino groups. It will be appreciated that where two or more $R^{10}$ substituents are present, these need not necessarily be the same atoms and/or groups. The $R^{16}$ substituents may be present at any ring carbon atom away from that attached to the rest of the molecule of formula (1). Thus, for example, in phenyl groups any substituents may be present at the 2-, 3- or 4- 5- or 6- positions relative to the ring carbon atom attached to the remainder of the molecule.

When the group $R^2$ in compounds of formula (1) is a substituted amino group, this may be for example a group —NHR$^{19}$ where $R^{19}$ is as defined above.

Esterified carboxyl groups represented by $R^2$ include groups of formula —CO$_2$R$^8$ where $R^8$ is as defined above.

When the groups $R^3$ and $R^4$ in compounds of formula (1) are alkyl groups, they may be for example $C_{1-6}$alkyl groups such as methyl or ethyl groups.

The group $R^5$ in compounds of formula (1) may be an optionally substituted straight or branched $C_{1-6}$alkyl, e.g. methyl, ethyl, n-propyl, i-propyl, n-butyl, i-butyl, n-pentyl or n-hexyl or $C_{2-6}$alkenyl e.g. ethenyl or 1-propenyl group optionally interrupted by one or more —O— or —S— atoms or —N(R$^7$)— groups where $R^7$ is a hydrogen atom or a $C_{1-6}$alkyl group such as a methyl group. Optional substitutents which may be present on alkyl or alkenyl groups $R^5$ include $C_{6-12}$aryl$C_{1-6}$alkyl groups such as optionally substituted phenyl$C_{1-6}$alkyl e.g. benzyl groups, $C_{6-12}$aryl$C_{1-6}$alkoxy groups such as optionally substituted phenyl$C_{1-6}$alkoxy e.g. benzyloxy groups, $C_{6-12}$aryl e.g. optionally substituted phenyl groups, $C_{3-8}$heteroaryl e.g. optionally substituted indole, imidazole or quinoline groups, $C_{6-12}$aryl$C_{1-6}$alkoxy$C_{6-12}$aryl, e.g. benzyloxyphenyl groups, —OH, —SH, $C_{1-6}$alkylthio e.g. methylthio or ethylthio, carboxyl (—CO$_2$H), amino (—NH$_2$), carboxamido (—CONH$_2$) or guanido —NHC(NH$_2$)=NH, groups. The optional substituents present on these groups may be $R^{10}$ substituents as discussed above.

When the group Alk is present in compounds of formula (1) it may be a straight or branched $C_{1-6}$alkyl, e.g. methyl, ethyl, n-propyl i-propyl, n-butyl, i-butyl, n-pentyl or n-hexyl or $C_{2-6}$alkenyl e.g. ethenyl or 1-propenyl group optionally interrupted by one or more —O— or —S— atoms or —N(R$^7$)— groups where $R^7$ is a hydrogen atom or a $C_{1-6}$alkyl group such as a methyl group.

The group $R^6$ in compounds of formula (1) may represent a $C_{3-8}$cycloalkyl, e.g. cyclopentyl or cyclohexyl, or $C_{3-8}$cycloalkenyl e.g. cyclopentenyl or cyclohexenyl, group optionally substituted by one, two or more $C_{1-6}$alkyl, e.g. methyl or ethyl, $C_{1-6}$alkoxy, e.g. methoxy or ethoxy, $C_{1-6}$alkylthio, e.g. methylthio, or hydroxyl groups.

The group X in compounds of formula (1) may be a group —NR$^{10}$R$^{11}$ where $R^{10}$ is a hydrogen atom or an optionally substituted $C_{1-6}$alkyl, e.g. methyl or ethyl, $C_{2-4}$alkanoyl, e.g. acetyl or propionyl, $C_{6-12}arC_{1-3}$alkyl, e.g. phen$C_{1-3}$alkyl such as benzyl or phenethyl, $C_{6-12}$ aryl e.g. phenyl, $C_{6-12}$ aroyl, e.g. benzoyl, or $C_{6-12}arC_{1-3}$alkanoyl, e.g phen$C_{1-3}$alkanoyl such as a methylphenylketone group and $R^{11}$ is a straight or branched $C_{1-6}$alkylaminosulphonylamino group wherein the alkyl portion is optionally interrupted by one or more —O— or —S— atoms or —N($R^7$)— or aminocarbonyloxy groups. Thus for example $R^{11}$ may be a group Alk$^1$N($R^7$)SO$_2$NR$^{12}$R$^3$ where Alk$^1$ is a $C_{1-6}$ alkyl group as just defined and wherein $R^{12}$ and $R^{13}$ which may be the same or different is each a hydrogen atom or an optionally substituted straight or branched alkyl group optionally interrupted by one or more —O— or —S— atoms or —N($R^7$)— or aminocarbonyloxy groups; or $R^{12}$ and $R^{13}$, together with the nitrogen atom to which they are attached, may form an optionally substituted $C_{3-6}$cyclic amino group optionally possessing one or more other heteroatoms, selected from —O— or —S—, or —N($R^7$)— groups.

The alkyl portion, Alk$^1$ of the alkylaminosulphonylamino group represented by $R^{11}$ may in particular be a methyl, ethyl, n-propyl, i-propyl, n-butyl, s-butyl or t-butyl group optionally interrupted by one or more —O— or —S— atoms or —N(RT) or aminocarbonyloxy groups and may be for example a methoxymethyl, ethoxymethyl, methoxyethyl, ethoxyethyl, or ethylaminocarbonyloxymethyl group.

When $R^{12}$ and/or $R^{13}$ is an alkyl group it may be for example a $C_{1-6}$alkyl group such as a methyl, ethyl, n-propyl, i-propyl, n-butyl, i-butyl, s-butyl, or t-butyl group, optionally interrupted by one or more —O— or —S— atoms, or —N($R^7$)— or aminocarbonyloxy groups and may be for example a methoxymethyl, ethoxymethyl, methoxyethyl, ethoxyethyl or ethylaminocarbonyloxymethyl group. The optional substituents which may be present on such groups include hydroxyl (—OH), carboxyl (—CO$_2$H), esterified carboxyl (—CO$_2$R$^{18}$), carboxamido (—CONH$_2$), substituted carboxamido, e.g. a group —CONR$^{12}$R$^{13}$ where NR$^{12}$R$^{13}$ is as defined herein, amino (—NH$_2$), substituted amino, for example a group of formula —NR$^{12}$R$^{13}$, or aryl, e.g. $C_{6-12}$ aryl such as phenyl, optionally substituted by one, two or more $R^{10}$ substituents selected from those listed above in relation to the group $R^2$.

Particular examples of cyclic amino groups represented by —NR$^{12}$R$^{13}$ include morpholinyl, imidazolyl, piperazinyl, pyrrolyl, oxazolyl, thiazolyl, pyrazolyl, pyrrolidinyl, pyridinyl and pyrimidinyl groups.

The groups $R^8$ or $R^9$ in compounds of formula (1) may be hydrogen atom or an optionally substituted straight or branched $C_{1-6}$alkyl, e.g. methyl, ethyl, n-propyl, i-propyl, n-butyl or i-butyl, $C_{6-12}$aryl e.g. phenyl, or $C_{6-12}$aryl$C_{1-6}$alkyl, e.g. benzyl, phenylethyl or phenylpropyl group. Optional substitutents present on alkyl groups of this type include one or more $C_{1-6}$alkoxy, e.g. methoxy, ethoxy, or $C_{1-6}$alkylthio e.g. methylthio or ethylthio groups or an optionally substituted $C_{6-12}$aryloxy, e.g. phenyloxy, $C_{6-12}$arylthio e.g. phenylthio, $C_{6-12}$aryl$C_{1-6}$alkoxy e.g. benzyloxy or $C_{6-12}$aryl$C_{1-6}$alkylthio e.g. benzylthio. Optional substituents present on the group $R^8$ or $R^9$ when it is an aryl or aralkyl group or an alkyl group substituted by an aryloxy or arylthio group include $R^{10}$ groups present on the cyclic part of $R^8$ or $R^9$ as defined above.

Salts of compounds of formula (1) include pharmaceutically acceptable salts, for example acid addition salts derived from inorganic or organic acids, such as hydrochlorides, hydrobromides, hydroiodides, p-toluene sulphonates, phosphates, sulphates, acetates, trifluoroacetates propionates, citrates, maleates, fumerates, malonates, succinates, lactates, oxalates, tartarates and benzoates.

Salts may also be formed with bases. Such salts include salts derived from inorganic or organic bases, for example alkali metal salts such as sodium or potassium salts, alkaline earth metal salts such as magnesium or calcium salts, and organic amine salts such as morpholine, piperidine, dimethylamine or diethylamine salts.

When the group R in compounds of the invention is an esterified carboxyl group, it may be a metabolically lablie ester of formula —CO$_2$R$^8$ where $R^{18}$ may be an ethyl, benzyl, phenylethyl, phenylpropyl, 1- or 2-naphthyl, 2,4-dimethylphenyl, 4-t-butylphenyl, 2,2,2-trifluoroethyl, 1-(benzyloxy)benzyl, 1-(benzyloxy)ethyl, 2-methyl-1-propionyloxypropyl, 2,4,6-trimethylbenzoyloxymethyl or pivaloyloxymethyl group.

When the group R in compounds of formula (1) is a —P(O)(X$^1$R$^8$)X$^2$R$^9$ group it may in particular be a —P(O)(OH)OR$^9$, —P(O)(SH)OR$^9$ or —P(O)(OH)SR$^9$ group. Examples of such groups include —P(O)(OH)OH, —P(O)(OH)SH, —P(O)(SH)OH, —P(O)(OH)OCH$_3$, —P(O)(OH)SCH$_3$, —P(O)(OH)OCH$_2$CH$_3$, —P(O)(OH)OPh, —P(O)(OH)SPh, —P(O)(OH)OCH$_2$Ph or —P(O)(OH)SCH$_2$Ph, where Ph is a phenyl group optionally substituted by one or more substituents $R^{10}$.

In the compounds of formula (1) the group $R^1$ may in particular be a $C_{1-6}$alkyl group such as a methyl group, an aralkyl group such as benzyl group, an arylthioalkyl group such as a phenylthiomethyl group or a heteroarylthioalkyl group such as thienylthiomethyl, pyridinylthiomethyl or pyrimidinylthiomethyl group or is especially a hydrogen atom.

The group $R^2$ may be in particular an optionally substituted $C_{1-6}$alkyl, $C_{3-8}$cycloalkyl, $C_{3-8}$cycloalkyl$C_{1-6}$alkyl, $C_{6-12}$aryl, $C_{6-12}$aryl$C_{1-6}$alkoxy or $C_{6-12}$aralkylthio group and, especially, a $C_{6-12}$aryl$C_{1-6}$alkyl group. Particular types of these groups are optionally substituted $C_{3-6}$ alkyl, such as n-propyl, i-propyl, n-butyl, i-butyl, s-butyl, t-butyl, n-pentyl or i-pentyl; cyclopentyl; cyclohexyl; cyclopentyl$C_{1-6}$alkyl, such as cyclopentyl$C_{3-6}$alkyl, e.g. cyclopentylpropyl, cyclopentylbutyl, or cyclopentylpentyl; phenyl; 1- or 2-naphthyl; phenyl$C_{1-6}$alkoxy, e.g. phenylethoxy, phenylpropoxy or phenylbutoxy; phenyl$C_{1-6}$ alkylthio, e.g. phenylethylthio, phenylpropylthio or phenylbutylthio; and, especially, phenyl$C_{1-6}$alkyl such as phenyl$C_{3-6}$alkyl e.g. phenylpropyl, phenylbutyl or phenylpentyl; or 1- or 2-naphthyl$C_{1-6}$alkyl such as 1- or 2-naphthyl$C_{3-6}$alkyl, e.g. 1- or 2-naphthylpropyl, naphthylbutyl or naphthylpentyl. Each of these cycloalkyl or aryl groups may be substituted, by one two or more substituents $R^{16}$ described above.

The groups $R^3$ and $R^4$ in compounds of formula (1) may each in particular be a methyl group, or, especially, a hydrogen atom.

The group $R^5$ in compounds of formula (1) may be in particular a group —AlkR$^6$, where $R^6$ is an optionally substituted cycloalkyl or cycloalkenyl group.

Thus, the group $R^5$ in compounds of formula (1) may be an optionally substituted $C_{3-8}$cycloalkyl$C_{1-6}$alkyl [e.g. cyclopentyl$C_{1-6}$alkyl such as cyclopentylmethyl or cyclopentylethyl, or cyclohexy$C_{1-6}$alkyl such as cyclohexylmethyl or cyclohexylethyl], $C_{3-8}$cycloalkenyl$C_{1-6}$alkyl [e.g. cyclopentenyl$C_{1-6}$alkyl such as cyclopentenylmethyl or cyclohexenyl$C_{1-6}$alkyl such as cyclohexenylmethyl], cycloalkyl$C_{1-3}$alkoxy$C_{1-3}$alkyl [e.g. cyclopentylmethoxymethyl, cyclohexylmethoxymethyl] $C_{3-8}$cycloalkenyl$C_{1-3}$alkoxy$C_{1-3}$alkyl [e.g. cyclopentenylmethoxymethyl or cyclohexenylmethoxymethyl] $C_{3-8}$cycloalkyl$C_{1-3}$alkylthio$C_{1-3}$alkyl [e.g. cyclopentylmethylthiomethyl or cyclohexylmethylthiomethyl] or $C_{3-8}$cycloalkenyl$C_{1-3}$alkylthio$C_{1-3}$alkyl [e.g. cyclopentenylmethylthiomethyl or cyclohexenylmethylthiomethyl], $C_{3-8}$cycloalky$C_{1-3}$alkylamino$C_{1-3}$alkyl [e.g. cyclopentylmethylaminomethyl, or cyclohexylmethylaminomethyl] or $C_{3-8}$cycloalkenyl$C_{1-3}$alkylamino$C_{1-3}$alkyl [e.g. cyclopentenylmethylaminomethyl or cyclohexenylmethytaminomethyl] group.

In another preference, the group $R^5$ in compounds of formula (1) may in particular be a $C_{1-6}$alkyl group, e.g. an i-propyl or i-butyl group, or an optionally substituted benzyl, benzyloxybenzyl or indolylmethyl group.

The group X in compounds of formula (1) is preferably a group $—NR^{10}R^{11}$ where $R^{10}$ is a hydrogen atom or an optionally substituted $C_{1-6}$alkyl group, such as methyl or ethyl group.

In another preference, the group X is preferably $—NR^{10}R^{11}$ where $R^{11}$ is an $Alk^1N(R^7)SO_2NR^{12}R^{13}$ group, wherein $Alk^1$ is straight or branched $C_{1-6}$alkyl optionally interrupted by one or more —O— or —S— atoms or —N($R^7$)— or aminocarbonyloxy groups. Compounds of this type where $Alk^1$ is a $C_{1-3}$ alkyl group, e.g. a methyl, ethyl or n-propyl group optionally interrupted by one or more —O— or —S— atoms or —N($R^7$)— [e.g. —NH— or —N($CH_3$)—] or aminocarbonyloxy groups are especially useful.

The group $—N(R^7)SO_2NR^{12}R^{13}$ in compounds of formula (1) may in particular be a group $—NHSO_2NR^{12}R^{13}$ or $—N(CH_3)SO_2NR^{12}R^{13}$.

In another group of compounds of formula (1) the group $—N(R^7)SO_2NR^{12}R^{13}$ may be for example a group $—N(R^7)SO_2NH_2$, $—N(R^7)SO_2NHR^{13}$ or $—N(R^7)SO_2NR^{12}R^{13}$ where $R^{12}$ and $R^{13}$ is each an optionally substituted $C_{1-6}$alkyl group or $R^{12}$ and $R^{13}$ together with the nitrogen atom to which they are attached is an optionally substituted $C_{3-6}$ cyclic amino group, for example a morpholinyl group.

A particularly useful group of compounds according to the invention is that of formula (1) wherein $R^5$ is an $AlkR^6$, group, where Alk is a $C_{1-6}$ alkyl and $R^6$ is a cycloalkyl or cycloalkenyl group.

Another particularly useful group of compounds according to the invention is that of formula (1) where $R^2$ is an optionally substituted alkyl, cycloalkyl, cycloalkylalkyl, aryl, aralkoxy or aralkylthio group.

In general, in compounds of formula (1) the groups $R^1$, $R^3$ and $R^4$ is each preferably a hydrogen atom.

In a further preference, the group R in compounds according to the invention is a —CONHOH or a —$CO_2H$ group or a metabolically labile ester thereof, or a group P(O)(OH)$OR^7$. In a particular preference, however, R is a —CONHOH, —$CO_2H$ or —P(O)(OH)$_2$ group.

An especially useful group of compounds according to the invention has the formula (1a).

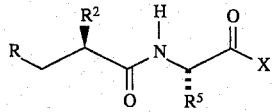

wherein R, $R^2$, $R^5$ and X are as defined for formula (1); and the salts, solvates and hydrates thereof.

A particularly useful group of compounds of formula (1a) are those wherein R represents a —CONHOH, or —$CO_2H$ or —P(O)(OH)$_2$ group; $R^2$ represents an optionally substituted alkyl, alkenyl, cycloalkyl, cycloalkylalkyl, aryl, aralkoxy or aralkylthio group;

$R^5$ represents a group —$AlkR^6$, where Alk is a $C_{1-6}$ alkyl group and $R^6$ is a cycloalkyl or cycloalkenyl group;

X is a group —$NR^{10}R^{11}$; and the salts, solvates and hydrates thereof.

Particularly useful compounds of formula (1a) are those wherein $R^5$ is a group —$AlkR^6$, and $R^6$ is an optionally substituted cyclohexyl group. Compounds of this type in which $R^5$ is a cyclohexyl$C_{1-6}$alkyl group.

Other useful compounds of formula (1a) include those wherein $R^2$ represents a $C_{3-6}$alkyl group, particularly an i-butyl or n-pentyl group, or a cycloalkyl$C_{3-6}$alkyl group, particularly a cyclohexylpropyl, cyclohexylbutyl or cyclohexylpentyl group, or especially an optionally substituted phenyl$C_{2-6}$alkyl group particularly an optionally substituted phenylethyl,phenylpropyl, phenylbutyl or phenylpentyl group. Optional substituents on the phenyl group may be one, two or more $R^{16}$ groups as defined for compounds of formula (1).

In the compounds of formula (1a) X may be a group —$NR^{10}R^{11}$ where $R^{11}$ is $Alk^1N(R^7)SO_2NR^{12}R^{13}$ and $R^{10}$ is a hydrogen atom or a $C_{1-6}$ alkyl group, especially a methyl or ethyl group. Particular compounds of this type are those wherein X is —$NHAlk^1N(R^7)SO_2NR^{12}R^{13}$.

An especially useful group of compounds according to the invention has the formula (1a) wherein $R^2$ is an optionally substituted phenyl$C_{3-6}$alkyl group, especially an optionally substituted phenylbutyl or in particular a phenylpropyl group; $R^5$ is a cyclohexylmethyl group; and X is a group —$NR^{10}R^{11}$, especially a group —$NHAlk^1N(R^7)SO_2NR^{12}R^{13}$.

In the compounds of formulae (1) and (1a), when the group $R^5$ is a cycloalkyl$C_{1-6}$alkyl group then the chiral centre to which this group is attached preferably has a S-configuration.

The compounds according to the invention may be prepared by the following processes. In the description and formulae below the groups R, $R^1$, $R^2$, $R^3$, $R^4$, $R^5$ and X are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable amino or hydroxyl protecting groups include benzyl, benzyloxycarbonyl or t-butyloxycarbonyl groups. These may be removed from a protected derivative by catalytic hydrogenation using for example hydrogen in the presence of a metal catalyst, for example palladium on a support such as carbon in a solvent such as an alcohol e.g. methanol, or by treatment with trimethylsilyl iodide or trifluoroacetic acid in an aqueous solvent. Suitable carboxyl protecting groups include benzyl groups, which may be removed from a protected derivative by the methods just discussed, or alkyl groups, such as a t-butyl group which may be removed from a protected derivative by treatment with trifluoroacetic acid in an aqueous solvent. Other suitable protecting groups and methods for their use will be readily apparent. The formation of the protected amino, hydroxyl or carboxyl group may be achieved using standard alkylation or esterification procedures, for example as described below.

Thus according to a further aspect of the invention a compound of formula (1) may be prepared by coupling an acid of formula (2)

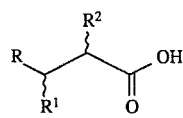

(2)

or an active derivative thereof, with an amine of formula (3)

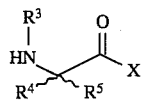

(3)

followed by removal of any protecting groups.

Active derivatives of acids for formula (2) include for example acid anhydrides, or acid halides, such as acid chlorides.

The coupling reaction may be performed using standard conditions for amination reactions of this type. Thus, for example the reaction may be achieved in a solvent, for example an inert organic solvent such as an ether, e.g. a cyclic ether such as tetrahydrofuran, an amide e.g. a substituted amide such as dimethylformamide, or a halogenated hydrocarbon such as dichloromethane at a low temperature, e.g. −30° C. to ambient temperature, such as −20° C. to 0° C., optionally in the presence of a base, e.g. an organic base such as an amine, e.g. triethylamine or a cyclic amine such as N-methylmorpholine. Where an acid of formula (2) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate for example ethylchloroformate, prior to reaction with the amine of formula (3).

Free hydroxyl or carboxyl groups in the starting materials of formulae (2) and (3) may need to be protected during the coupling reaction. Suitable protecting groups and methods for their removal may be those mentioned above. Where R in the intermediates of formula (2) is a $-P(O)(X^1R^8)X^2R^9$ group, at least one of $R^8$ or $R^9$ is other than a hydrogen atom. Conveniently, each of $R^8$ and $R^9$ is a optionally substituted alkyl, aryl or aralkyl group. Such groups, when present in compounds of the invention may be cleaved as described below to yield other compounds of the invention wherein $R^8$ and/or $R^9$ is each a hydrogen atom.

It will be appreciated that where a particular steroisomer of formula (1) is required, this may be obtained by resolution of a mixture of isomers following the coupling reaction of an acid of formula (2) and an amine of formula (3). Conventional resolution techniques may be used, for example separation of isomers by Chromatography e.g. by use of high performance liquid chrormatography. Where desired, however, appropriate homochiral staring materials may be used in the coupling reaction to yield a particular stereo isomer of formula (1). Thus, in a particular process a compound of formula (1a) may be prepared by reaction of a compound of formula (2a)

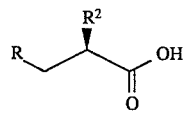

(2a)

with an amine of formula (3a)

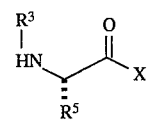

(3a)

as described above.

Intermediate acids of formula (2) wherein R is a carboxyl or esterified carboxyl group or a group $-P(O)(X^1R^8)X^2R^9$ may be prepared from a corresponding ester of formula (4)

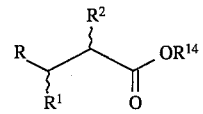

(4)

where $R^{14}$ is an alkyl group, for example a methyl or t-butyl group, by hydrolysis using for example trifluoroacetic acid, or, when $R^{14}$ is an aralkyl group, such as a benzyl group, by hydrogenolysis, for example by reaction with hydrogen in the presence of a metal catalyst, e.g. palladium, on a support such as carbon in a solvent such as an alcohol, e.g. methanol optionally at an elevated pressure and temperature.

An ester of formula (4) where R is a carboxyl or esterified carboxyl group may be prepared by esterification of the corresponding acid of formula (5)

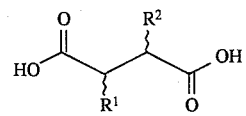

(5)

using an appropriate acyl halide, for example an acyl chloride in a solvent such as an alcohol, e.g. methanol at a low temperature, e.g. around 0° C.

Acids of formula (5) may be prepared by alkylation of a compound of formula (6)

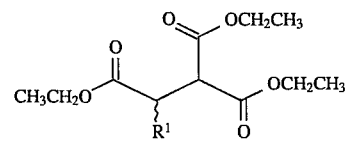

(6)

with an appropriate halide, e.g. a compound $R^2$Hal, where Hal is a halogen atom such as a chlorine or bromine atom in the presence of a base, for example an alkoxide such as sodium ethoxide in a solvent such as an alcohol, e.g. ethanol at ambient temperature, followed by decarboxylation using for example concentrated hydrochloric acid at an elevated temperature, e.g. the reflux temperature.

Intermediates of formula (6) are either known compounds or may be prepared by methods analogous to those used for the preparation of the known compounds.

Intermediate esters of formula (4) where R is a $-P(O)(X^1R^8)X^2R^9$ group may be prepared by reaction of an acrylate $R^1CHC(R^2)COR^{14}$ with a phosphite $-P(OR^{15})(X^1R^8)X^2R^9$ [where $R^{15}$ is a leaving group, for example a silyl group such as a trialkylsilyl group e.g. a trimethylsilyl group] at an elevated temperature.

Acrylates of formula $R^1CHC(R^2)COR^{14}$ may be prepared by reaction of a mono-ester $HOOCCH(R^2)COOR^{14}$ with an aldehyde $R^1CHO$ or a polymer thereof e.g. paraformaldehyde or paraldehyde in the presence of a base, for example an organic base such as piperidine. The reaction may be performed in a solvent, such as pyridine, optionally at an elevated temperature.

Mono-esters of formula $HOOCCH(R^2)COOR^{14}$ may be prepared by hydrolysis of the corresponding di-ester $R^{14}OOCCH(R^2)COOR^{14}$ using a base, for example an alkali hydroxide, in an inert solvent such as dioxan at a low temperature e.g. around 0° C. The di-esters for use in this reaction may be prepared by alkylation of the corresponding malonates of formula $R^{14}OOCCH_2COOR^{14}$ with a halide $R^2Hal$ [where Hal is a halogen atom such as a chlorine or bromine atom] in the presence of a base, e.g. a hydride such as sodium hydride in a solvent such as tetrahydrofuran at ambient temperature. Malonates of formula $R^{14}OOCCH_2COOR^{14}$ are either known compounds or may be prepared by methods analogous to those used for the preparation of the known compounds.

Intermediate phosphites of formula $-P(OR^{15})(X^1R^8)X^2R^9$ may be prepared by reaction of a phosphite $-P(O)(X^1R^8)X^2R^9$ with an appropriate amine $(R^{15})_2NH$ e.g. a silazane, at an elevated temperature, e.g. the reflux temperature. Phosphites of formula $P(O)(X^1R^8)X^1R^9$ are either known compounds or may be prepared by methods analogous to those used for the preparation of the known compounds.

Intermediate acids of formula (4) wherein R is a —CONHOH group or a protected derivative thereof may be prepared by reaction of an anhydride of formula (7)

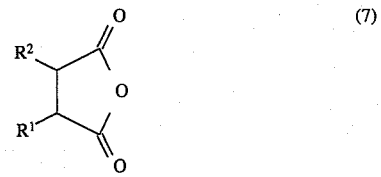

with a hydroxylamine such as O-benzylhydroxylamine in a solvent such as tetrahydrofuran at a low temperature, e.g. around −20° C., followed where desired by removal of the protecting group as described above.

The intermediate anhydrides of formula (7) may be prepared for example by heating for example at the reflux temperature, a diacid of formula (5) where R is —$CO_2H$ with an acyl chloride such as acetyl chloride.

Intermediate amines of formula (3) may be prepared by reaction of the corresponding acids $R^3NHC(R^4)(R^5)COOH$ or active derivatives thereof with an amine XH using the reagents and conditions described above for the preparation of compounds of formula (1) from intermediates for formula (2) and (3). The acids $R^3NHC(R^4)(R^5)COOH$ and amines XH are either known compounds or may be prepared from known starting materials using analogous processes [for example as described in the preparation of the specific Intermediates in the Examples herein] to those used for the preparation of the known compounds.

The homochiral acids of formula (2a) may be prepared according to another feature of the invention by oxidation of an oxazolidinone of formula (8)

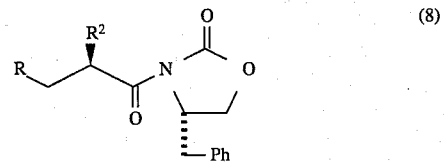

(where Ph is a phenyl group)
using an oxidising agent such as peroxide, e.g. hydrogen peroxide in a solvent such as an ether e.g. a cyclic ether such as tetrahydrofuran, at a low temperature, e.g. around 0° C. followed by treatment with a base, such as lithium hydroxide, at an elevated temperature.

The compounds of formula (8) are novel, particularly useful, intermediates for the preparation of stereoisomers of formula (1a) and form a further aspect of the invention.

The compounds of formula (8) may be prepared by reaction of an acyl halide $(R^2)COHal$ (where Hal is a halogen atom such as chlorine, bromine or iodine atom) with a solution of (S)-4-(phenylmethyl)- 2-oxazolidinone in the presence of a base such as n-butyl lithium in a solvent such as tetrahydrofuran at a low temperature, e.g. around −78° C., followed by treatment of the resulting oxazolidinone with a reagent $RCH_2Hal$ in the presence of a silazide such as sodium hexamethyldisilazide at a low temperature.

Acyl halides $R^2COHal$ may be prepared by treatment of the corresponding known acids $R^2CO_2H$ with conventional halogenating agents for example thionyl halides under standard reaction conditions.

In another process according to the invention, a compound of formula (1) where R is a carboxyl group may be prepared by decarboxylation of a corresponding compound of formula (9)

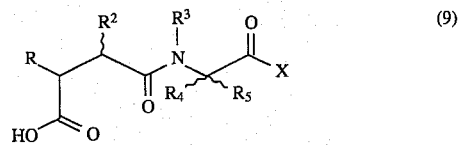

The reaction may be achieved using standard conditions, for example by heating a compound of formula (9) in an inert solvent, such as an aromatic hydrocarbon, e.g. xylene, at the reflux temperature.

The intermediate acids of formula (9) may be prepared by reaction of a protected acid of formula (10)

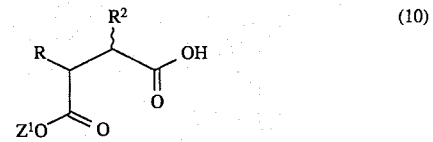

where R is a protected carboxyl group such as a benzyloxycarbonyl group and $Z^1$ is a protecting group such as a benzyl group with an amine of formula (3) using reagents and conditions as described above for coupling compounds of formula (2) and (3), followed by removal of the protecting groups.

The intermediates of formula (10) may be prepared by treatment of an appropriate malonic ester $RCH_2CO_2Z^1$ with a halide of formula (11)

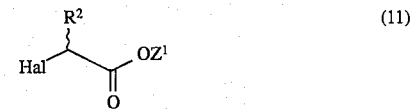

(where Hal is a halogen atom, e.g. a chlorine or bromine atom) in the presence of a base such as potassium t-butoxide in a solvent such as dimethylformamide at ambient temperature.

Halides of formula (11) may be prepared by halogenation and subsequent decarboxylation of a di-acid of formula (12).

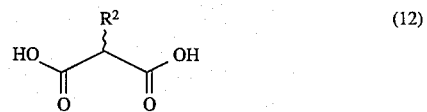

using for example a halogenating agent such as bromine in a solvent such as diethyl ether at ambient temperature, followed by heating of the resulting halogenated intermediate in a solvent such as an aromatic hydrocarbon e.g. xylene, at the reflux temperature.

Intermediates of formula (12) may be prepared by hydrolysis of the corresponding di-alkylester (e.g. the dimethyl or diethyl ester) using a base such as sodium or potassium hydroxide in a solvent such as an alcohol e.g. methanol at the reflux temperature. The di-alkyl ester starting materials are either known compounds or may be prepared by methods analogous to those used for the preparation of the known compounds, for example as described in the Examples herein.

Compounds of formula (1) may also be prepared by interconversion of other compounds of formula (1). Thus, for example, a compound of formula (1) wherein R is a —CONHOH group may be prepared by reaction of a corresponding acid of formula (1) wherein R is a —$CO_2H$ group or an active derivative thereof (for example an acid chloride or an acid anhydride) with hydroxylamine or an O-protected derivative for example O-trimethylsilylhydroxylamine or a salt thereof. The reaction may be performed using the reagents and conditions described above in the preparation of compounds of formula (1) from the starting materials of formulae (2) and (3). If desired the acid starting material may be reacted with a chloroformate, for example ethyl chloroformate, prior to reaction with the hydroxylamine or protected hydroxylamine.

In another interconversion process, compounds of formula (1) wherein R is —$CO_2H$ may be prepared by hydrolysis of the corresponding esterified compounds (for example where R is a —$CO_2R^{18}$ group and/or X contains a similar group) using conventional procedures, for example by treatment with a base, e.g. an alkali metal hydroxide such as lithium hydroxide in a solvent such as an aqueous alcohol, e.g. aqueous methanol, or by treatment with an acid such as a mineral acid, e.g. hydrochloric acid in the presence of a solvent, e.g. dioxan.

Similarly esters of formula (1), for example where R is a $CO_2R^{18}$ group and/or X contains a —$CO_2R^{18}$ group may be prepared by reaction of the corresponding acids, where R is a —$CO_2H$ group and/or X contains a —$CO_2H$ group or an active derivative thereof, with an alcohol $R^{18}OH$ using standard conditions.

The compounds according to the invention are potent and selective inhibitors of gelatinase. The activity and selectivity of the compounds may be determined by the use of appropriate enzyme inhibition test for example as described in Example A hereinafter. In our tests using this approach, compounds according to the invention have been shown to inhibit gelatinase with Ki values in the picomolar-nanomolar range and to have around a 40 fold or greater selectivity for gelatinase over stromelysin, and around a 100-fold or greater selectivity for gelatinase over collagenase.

The ability of compounds of the invention to prevent tumour cell invasion may be demonstrated in a standard mouse model.

Thus, briefly, nude mice may be inoculated with a tumour cell line showing gelatinase—dependent invasion and the ability of compounds according to the invention to reduce subsequent lung tumour colonisation may be evaluated in accordance with standard procedures. In out tests, compounds according to the invention, when administered intravenously at 1 mg/kg to mice in the above model have reduced lung tumour colonisation to neglagable levels.

The compounds according to the invention can be expected to be of use to prevent tumour cell metastasis and invasion. The compounds may therefore be of use in the treatment of cancer, particularly in conjunction with radiotherapy, chemotherapy or surgery, or in patients presenting with primary tumours, to control the development of tumour metastasis. Thus, according to a further aspect of the invention we provide a compound of formula (1) for use in the treatment of cancer to control the development of tumour metastasis. Particularly cancers may include breast, melanoma, lung, head, neck or bladder cancers.

For use according to this aspect of the invention, the compounds of formula (1) may be formulated in a conventional manner, optionally with one or more physiologically acceptable carriers, diluents or excipients.

Thus according to a further aspect of the invention we provide a pharmaceutical composition comprising a compound of formula (1) and a pharmaceutically acceptable diluent, carrier or excipient.

In a still further aspect the invention provides a process for the production of a pharmaceutical composition comprising bringing a compound of formula (1) into association with a pharmaceutically acceptable diluent, carrier or excipient.

Compounds for use according to the present invention may be formulated for oral, buccal, parenteral or rectal administration or in a form suitable for nasal administration or administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles; and preservatives. The preparations may also contain buffer salts, flavoring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parenteral administration by injection e.g. by bolus injection or continuous infusion. Formulations for injection may be presented in unit dosage form. The compositions for injection may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (1) may also be formulated in rectal compositions such as suppositories or retention enemas, e.g. containing conventional suppository bases such as cocoa butter or other glycerides.

In addition to the formulations described above the compounds of formula (1) may also be formulated as a depot preparation. Such long acting formulations may be administered by implantation or by intramuscular injection.

For nasal administration or administration by inhalation the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas.

The compositions may, if desired, be presented in a pack or dispenser device which may contain one or more unit dosage forms containing the active ingredient. The pack or dispenser device may be accompanied by instructions for administration.

The doses of compounds of formula (1) used to control the development of tumour metastases will vary depending on the condition of the patient to be treated but in general may be in the range around 0.5 mg to 100 mg/kg body weight, particularly from about 1 mg to 40 mg/kg body weight. Dosage units may be varied according to the route of administration of the compound and condition of the patient in accordance with conventional practice.

The following Examples illustrate the invention.

EXAMPLE A

The activity and selectivity of the compounds of the invention may be determined as described below.

All enzyme assays to determine Ki values were performed using the peptide substrate Dnp-Pro-Leu-Gly-Trp-Ala-D-Arg—$NH_2$. [M. Sharon Stock and Rober D. Gray, JBC 264, 4277–81, 1989]. The enzymes cleave at the Gly-Leu bond which can be followed fluorimetrically by measuring the increase in Trp fluorescence emission associated with the removal of the quenching dinitrophenol (Dnp) group.

Essentially, enzyme (e.g. gelatinase, stromelysin, collagenase) at 0.08–2 nM; a range of inhibitor concentrations (0.1–50×Ki) and substrate (approx. 20 μm) are incubated overnight in 0.1M Tris/HCl buffer, pH 7.5, containing 0.1M NaCl, 10 mM $CaCl_2$ and 0.05%. Brij 35 at either room temperature or 37° C. depending on the enzyme. The reaction is stopped by adjusting the pH to 4 using 0.1M sodium acetate buffer and the fluorescence read at an excitation wavelength of 280 nm and emission wavelength of 346 nm.

$K_i$ values can be established using the equation for tight-binding inhibition:

$$V_i = \frac{V_o}{2[E]} (\sqrt{(K_{i(app)} + [I])^2 + 2(K_{i(app)} - [I])[E] + [E]^2} - (K_{i(app)} + [I] - [E]))$$

where $V_o$ is the initial rate of reaction in the absence of inhibitor, $V_i$ is the initial rate in the presence of inhibitor, [E] is the total enzyme concentration and [I] the total inhibitor concentration in the reaction mixture.

For stromelysin and collagenase, $K_i$ (app) was assumed to approximate to the true $K_i$ as [S]<<$K_m$ for the substrate hydrolysis. For gelatinase the $K_i$ was determined by performing the analyses at several substrate concentrations. A plot of $K_i$(app) vs. [S] then gave the true $K_i$ as the value of the y-axis intercept.

The following results were obtained with compounds according to the invention.

| Compound of Example No. | Ki (nM) | | |
|---|---|---|---|
| | Collagenase | Stromelysin-1 | Gelatinase 72KD |
| 2 | 100000 | 802 | 1.43 |
| 3 | 385 | 2.75 | 0.01 |
| 4 | 302 | 1.73 | 0.014 |

| Compound of Example No. | Ki (nM) | | |
|---|---|---|---|
| | Collagenase | Stromelysin-1 | Gelatinase 72KD |
| 5 | 554 | 18.7 | 0.047 |
| 6 | 800 | 6.8 | 0.01 |

The following abbreviations are used in the description of the preparation of Intermediates and in the Examples:

| | |
|---|---|
| THF | tetrahydrofuran |
| EtOAc | ethyl acetate |
| DCCI | dicyclohexylcarbodiimide |
| MeOH | methanol |
| TFA | trifluoroacetic acid |
| $NEt_3$ | triethylamine |
| RT | room temperature |
| DMF | dimethylformamide |
| EDC | 1-(3-dimethylaminopropyl)-3-ethylcarbodiimide hydrochloride |

INTERMEDIATE 1

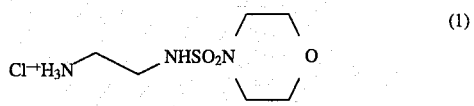

(1)

Morpholine sulphonyl chloride (10 g; 53.9 mmol) was added dropwise to ethylene diamine (200 ml) and stirred at RT for 3 hours. Excess ethylene diamine was evaporated under reduced pressure, the residue was taken up in 1N HCl and the solvent was removed. The pale brown solid was extracted with MeOH and the insoluble precipitate of ethylene aliamine dihydrochioride was filtered off. The filtrate was evaporated to give the desired sulphonyl urea (1) as a pale brown solid (9.5 g).

$^1$Hnmr ($D_2O$) δ3.8 (4H, t); 3.45 (2H, t); 3.25 (4H, t); 3.15 (2H, t).

INTERMEDIATE 2

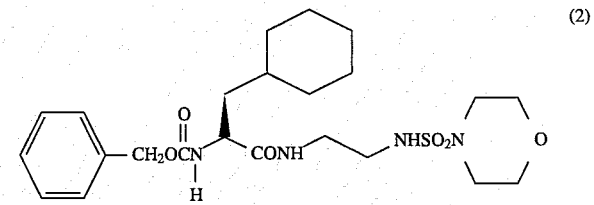

(2)

To a solution in dry DMF (50 $cm^3$) of N-CBZ-cyclohexylalanine (3.05 g, 10 mmol) was added N-methylmorpholine (2.31 $cm^3$, 21 mmol), Intermediate 1 (2.35 g, 9.57 mmol), 1-hydroxybenzotriazole (20 $cm^3$ of 0.5N solution in DMF, 10 mmol) and EDC (1.97 g, 10 mmol). The reaction mixture was stirred at room temperature for 18 hours then partitioned between diethyl ether and aqueous sodium carbonate solution. The organic layer was separated and washed with aqueous citric acid solution followed by water. The organic layer was separated, dried ($MgSO_4$) and evaporated. The residue was chromatographed on silica, eluting with 3% MeOH in $CH_2Cl_2$, to give the product (2) as a white solid (3.7 g).

$^1$Hnmr ($CDCl_3$) δ:7.2–7.4 (6H, m); 5.9 (2H, m); 5.1 (2H, dd); 4.2 (1H, dd); 3.7 (4H, t); 3.1–3.5 (8H, m); 0.8–1.8 (13H, m).

INTERMEDIATE 3

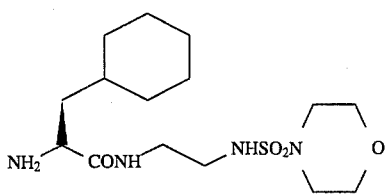
(3)

Intermediate 2 (2.99 g, 5.8 mmol) was dissolved in MeOH (100 cm³) and 10% palladium on carbon catalyst was added. The reaction mixture was stirred at room temperature under an atmosphere of hydrogen for 3 hours. The catalyst was filtred off and the filtrate was evporated to give the amine (3) as a clear gum (2.1 g).

1Hnmr (CDCl₃) δ: 8.3 (1H, br s); 6.9–7.6 (2H, m); 4.2 (1H, t); 3.6–3.9 (6H, m); 3.1–3.4 (6H, m); 0.9–1.9 (15H, m).

INTERMEDIATE 4

2-(R)-[3-(4-methylphenyl)propyl]succinic acid-4-t-butyl monoester (a) (S)-3[1-oxo-5-(4-methylphenyl)pentyl]-4-(phenylmethyl)-2-oxazolidinone (1)

BuLi (1.6M solution in hexanes, 4.4 mmol, 2.75 ml, 1.2 equiv.) was added dropwise to a solution of (S)-4-(phenylmethyl)-2-oxazolidinone (3.64 mmol, 0.64 g) in THF (15 ml) at −78° C., under N₂ atmosphere. The orange solution was stirred for 30 mins at −78° C. and then a solution of p-toylvalerylchloride (4.06 mmol, 0.86 g) in THF (5 ml) was added dropwise. The reaction mixture was stirred at −78° C. for 2 hrs before quenching at −78° C. with a mixture of brine and 10% aqueous HCl (1:1, 20 ml). On warming to ambient temperature the reaction mixture was partitioned between EtOAc and water. The aqueous layer was separated and extracted twice with EtOAc. The combined organic layers were washed once with brine, once with sodium bicarbonate solution and dried over MgSO₄. The solvent was removed under vacuum to give a brown oil which was purified on silica gel (Merck 9385) eluting with 20% EtOAc/hexane to give the compound as a slightly yellow oil (0.65 g, 51%).

¹Hnmr (CDCl₃) δ: 1.63 (m, 4H); 2.31 (s, 3H); 2.62 (m, 2H); 2.75 (dd, 1H); 2.89–2.98 (m, 2H); 3.26 (dd, 1H); 4.12–4.18 (m, 2H); 4.61–4.67 (m, 1H); 7.17–7.36 (m, 9H).

(b) 3-[1-oxo-2(R)(t-butylacetyl)-5-(4-methylphenyl)pentyl]-4-(S)-phenylmethyl- 2-oxazolidinone (2)

A solution of the oxazolidinone (1) (0.65 g, 1.85 mmol) in THF (10 ml) was added to a solution of sodium bis(trimethylsilyl)azide (1M Solution in THF, 2.6 mmol, 2.6 ml, 1.4 equiv.) in THF (10 ml) at −78° C. under nitrogen. The reaction mixture was stirred at this temperature for 1 hr and then t-butylbromoacetate (5.6 mmol, 1.08 g, 0.90 ml, 3 equiv.) was added dropwise. The reaction was allowed to warm to −20° C. over 4 hours. The reaction was quenched at −78° C. with a mixture of brine and 10% HCl (1:1, 20 ml). The mixture was partitioned between EtOAc and water. The aqueous layer was separated and extracted twice with EtOAc. The combined EtOAc layers were washed once with brine and once with NaHCO₃ solution and dried over MgSO₄. The solvent was removed to give a yellow oil, which was purified on silica gel (Merck 9385) eluting with 20% EtOAc/hexane to give the compound (2) (0.57, 66%).

¹Hnmr (CDCl₃) δ: 1.42 (s, 9H); 1.57–1.62 (m, 2H); 2.30 (s, 3H); 2.41–2.85 (m, 5H); 3.33 (dd, 1H); 4.10–4.25 (m, 1H); 7.01–7.09 (m, 4H); 7.22–7.37 (m, 5H).

(c) 2-(R)-[3-(4-methylphenyl)propyl]succinic acid-4-t-butyl monoester (3)

A solution of the oxazolidinone (2) (0.57 g, 1.23 mmol) in THF/water (4:1,25 ml) was cooled in an ice bath and treated with hydrogen peroxide solution (27.5 wt %, 4.9 mmol, 0.56 ml, 4 equiv). The mixture was stirred for a few minutes then a solution of lithium hydroxide monohydrate (1.23 mmol, 52 mg, 1.0 equiv.) in water (5 ml) was added dropwise. The reaction was stirred for 90 mine then treated with a 10% aqueous solution of sodium sulphite (5 ml). The reaction mixture was adjusted to pH 12–13 with 1M NaOH and then partitioned between dichloromethane and water. The aqueous layer was separated and acidified with 10% HCl. The aqueous layer was extracted three time with EtOAc. The combined organic layers were washed once with brine, once with NaHCO₃ solution and dried over MgSO₄ and the solvent removed to give the compound (3) as a yellowish oil (0.18 g, 48%), which was used without further purification.

¹Hnmr (CDCl₃) δ: 1.43 (s, 9H); 1.51–1.79 (m, 4H); 2.32 (2, 3H); 2.37 (dd, 1H); 2.82 (m, 1H); 7.03–7.12 (m, 4H).

EXAMPLE 1

{4-t-butoxy-2(R)-[3-(4-methylphenyl)propyl]succinyl}-L-β-cyclohexylalanine-N-[(2-morpholinesulphonylamino-)ethyl]amide

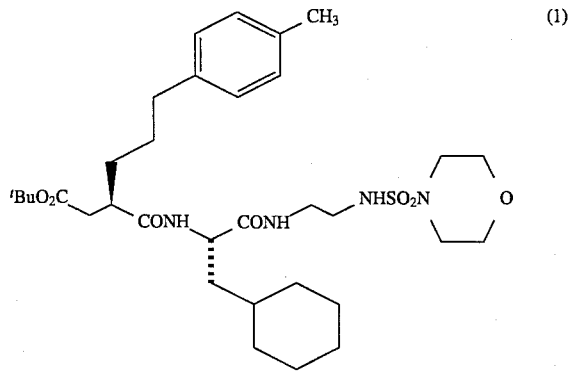
(1)

A solution of Intermediate 4 (0.2 g) in THF (10 ml) was treated with N-methyl morpholine (0.62 mmol, 62.2 mg, 67.7 µl) and cooled to −20° C. under N₂. The mixture was then treated with ethyl chloroformate (0.59 mmol, 64.1 mg, 56.5 µl) and stirred at −20° C. for 1 hour during which time a white precipitate formed. After this time a solution of Intermediate 3 (150 mg) in THF (5 ml) was added dropwise and the reaction allowed to warm to ambient temperature overnight. The reaction was partitioned between EtOAc and water. The aqueous layer was separated and extracted twice with EtOAc. The combined EtOAc layers were washed once with 10% HCl, once with NaHCO₃ and once with brine, dried over MgSO₄ and the solvent removed under vacuum to give an oil which was purified on silica gel (Merck 9385) eluting with 1% MeOH/CH₂Cl₂ to give 0.16 g of the title compound as a slightly yellow oil.

¹Hnmr (CDCl₃) δ: 7.05 (4H, 2d); 6.25 (1 H, br d); 5.55 (1H, Br t); 4.30 (1H, m); 3.75 (4H, t); 3.1–3.5 (BH, m); 2.4–2.7 (5H, m); 2.3 (3H, s); 0.8–1.8 (26H, m).

EXAMPLE 2

{4-Hydroxy-2-(R)-[3-(4-methylphenyl)propyl]succinyl}-L-β-cyclohexylalanine-N-[(2-morpholinesulphonylamino)ethyl]amide

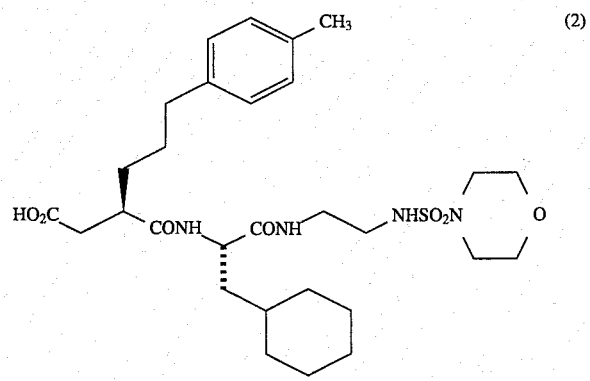

The t-butylester of Example 1 (0.2 g) was treated with water (0.5 ml) and TFA (2.5 ml) and allowed to stand overnight (18 h). The volatiles were removed under vacuum to give an oil which solidified on standing. Trituration with diisopropyl ether gave the title compound (2) as powdery solid.

$^1$Hnmr (CDCl$^3$) δ: 7.5 (1H, t); 70.5 (4H, d); 4.4 (1H, m); 3.75 (4H, t); 3.1–3.6 (8H, m); 2.5–2.8 (5H, m); 2.3 (3H, s); 0.8–1.8 (17H, m).

EXAMPLE 3

{4-(N-Hydroxyamino)-2-(R)-[3-(4-methylphenyl)propyl]succinyl}-L-β-cyclohexylalanine-N-[(2-morpholinesulphonylamino)ethyl]amide

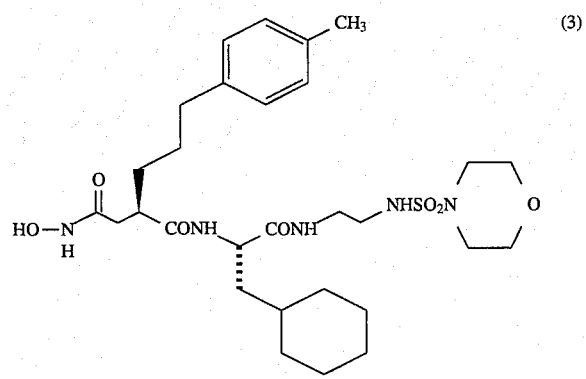

The compound of Example (2) (405 mg, 0.68 mmol) was dissolved in dry THF (5 cm$^3$) and cooled to −20° C. N-methylmorpholine (89 μl, 0.80 mmol) and ethyl chloroformate (72 μl, 0.75 mmol) were added and the reaction mixture was stirred at −16° C. for 1 hour. O-trimethylsilylhydroxylamine (360 μl, 3.4 mmol) was added dropwise and the reaction mixture was allowed to warm to room temperature overnight. The solvent was evaporated under reduced pressure and the residue was partitioned between EtOAc and aqueous citric acid. The organic layer was separated, dried (MgSO$_4$) and evaporated. The desired hydroxamic acid (3) was purified by reverse phase HPLC (Dynanax C18 column), eluting at 15.3 minutes under a 40→60% acetonitrite in water gradient. Yield: 220 mg.

$^1$Hnmr (CD$_3$OD) δ: 7.05 (4H, s); 4.25 (1H, dd); 3.70 (4H, t); 3.1–3.4 (8H, m); 2.5–2.8 (3H, m); 2.40 (1H, dd); 2.30 (3H, s); 2.25 (1H, dd); 0.8–1.8 (17H m).

The following compounds were made following the general teaching Example 3 using the analogous starting materials.

EXAMPLE 4

{4-(N-Hydroxyamino)-2-(R)-[3-(4-chlorophenyl)propyl]succinyl}-L-β-cyclohexylalanine-N-[(2-morpholinesulphonylamino)ethyl]amide

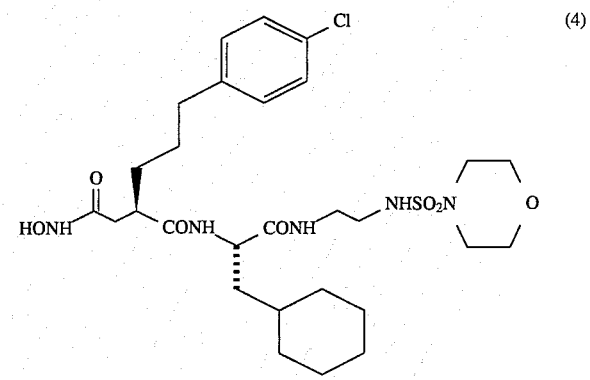

$^1$Hnmr (CD$_3$OD) δ: 8.20 (1H, m); 7.25 (2H, d); 7.16 (2H, d); 4.29 (1H, m); 3.70 (4H, m); 3.32 (2H, m); 3.11 (6H, m); 2.72 (1H, m); 2.60 (2H, m); 2.40 (1H, dd); 2.20 (1H, dd); 1.9–0.8 (17H, m).

EXAMPLE 5

{4-(N-Hydroxyamino)-2-(R)-[3-(4-methylphenyl)propyl]succinyl}-L-β-(1-cyclohexenylalanine)-N-[(2-morpholinesphonylamino)ethyl]amide

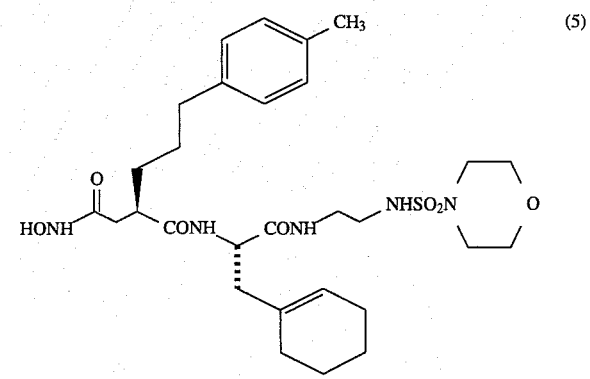

$^1$Hnmr (CD$_3$OD) δ: 7.05 (4H, m); 5.50 (1H, m); 4.35 (1H, m); 3.70 (4H, t); 3.30 (2H, m); 3.15 (6H, m); 2.75–2.20 (8H, m); 2.0–1.35 (14H, m).

EXAMPLE 6

{4-(N-Hydroxyamino)-2-(R)-[3-(4-methylphenyl)propyl]succinyl}-L-β-cyclohexylalanine-N-[(2-dimethylsulphonylamino)propyl]amide

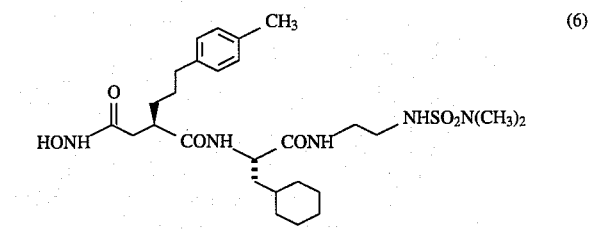

¹Hnmr (CD₃OD) δ: 7.05 (4H, m); 4.30 (1H, m); 3.30 (2H, m); 3.10 (2H, t); 2.7–2.8 (7H, m); 2.60 (2H, m); 2.40 (1 H, dd); 2.25 (3H, s); 2.20 (1H, dd); 1.8–0.9 (17H, m).

We claim:

1. A compound of formula (1):

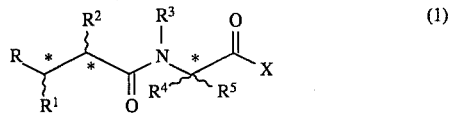

wherein R represents a —CONHOH, carboxyl (—CO₂H), —CO₂R¹⁸ wherein R¹⁸ is a straight or branched $C_{1-8}$ alkyl, benzyl, phenylethyl, phenylpropyl, 1-naphthylmethyl, 2-naphthylmethyl, phenyl, 1-naphthyl, 2-naphthyl phenyloxymethyl, phenyloxyethyl, 1-naphihyloxymethyl, 2-naphthyloxymethyl, $C_{1-8}$alkanoyloxy$C_{1-8}$alkyl, benzoyloxyethyl or benzoyloxypropyl group, each being unsubstituted or substituted by one or more halogen atoms or $C_{1-4}$alkyl or $C_{1-4}$alkoxy groups or —P(O)(X¹R⁸)X²R⁹ group, where X¹ and X², which are the same or different, is each an oxygen or a sulphur atom, and R⁸ and R⁹, which are the same or different, each represents a hydrogen atom or a $C_{1-6}$alkyl, phenyl, benzyl, phenylethyl or phenylpropyl group;

R¹ represents a hydrogen atom or a straight or branched $C_{1-6}$ alkyl or $C_{2-6}$alkenyl group, each being unsubstituted or substituted by one or more $C_{1-6}$alkoxy, $C_{1-6}$alkylthio, phenyl$C_{1-6}$alkoxy, phenyl$C_{1-6}$alkylthio, amino (—NH₂), carboxyl (—CO₂H), —CO₂R¹⁸, or —NHR¹⁹ group, where R¹⁹ is a $C_{1-6}$alkyl, phenyl$C_{1-6}$alkyl, phenyl, $C_{3-8}$cycloalkyl, or $C_{3-8}$cycloalkyl$C_{1-6}$alkyl group;

or R¹ is a phenyl, 1- or 2-naphthyl, phenyl$C_{1-6}$alkyl, 1- or 2-naphthyl$C_{1-6}$alkyl, $C_{3-6}$heteroaryl$C_{1-6}$alkyl, or $C_{3-6}$heteroarylthio$C_{1-6}$alkyl group, each of said phenyl, naphthyl or heteroaryl groups being unsubstituted or substituted by one or two substituents R¹⁶, where R¹⁶ represents a halogen atom or a $C_{1-6}$alkyl, $C_{2-6}$alkylenedioxy, halo$C_{1-6}$alkyl, $C_{1-6}$ alkylamino, $C_{1-6}$ dialkylamino, amino (—NH₂), nitro, cyano, hydroxyl (—OH), carboxyl (—CO₂H), —CO₂R¹⁸, $C_{1-6}$alkylcarbonyl, —SO₃H, $C_{1-6}$ alkylsulphonyl, sulphonamide (—SO₂NH₂), $C_{1-6}$ alkylaminosulphonyl, $C_{1-6}$ dialkylaminosulphonyl, carboxamido (—CONH₂), $C_{1-6}$ alkylaminocarbonyl, $C_{1-6}$ dialkylaminocarbonyl, sulphonylamino (—NHSO₂H), or $C_{1-6}$ alkylsulphonylamino groups;

R² represents a straight or branched $C_{1-6}$alkyl or $C_{2-6}$alkenyl group, unsubstituted or substituted by one or more $C_{1-6}$alkoxy, $C_{1-6}$alkylthio, phenyl$C_{1-6}$alkoxy, phenyl$C_{1-6}$alkylthio, amino (—NH₂), carboxyl (—CO₂H) or —CO₂R¹⁸ groups; or R₂ is a phenyl, 1- or 2-naphthyl, phenyl$C_{1-6}$alkyl, 1- or 2-naphthyl$C_{1-6}$alkyl, $C_{3-8}$cycloalkyl, $C_{3-8}$cycloalkyl$C_{1-6}$alkyl, phenyl$C_{1-6}$alkoxy or phenyl$C_{1-6}$alkythio group, each of said phenyl, naphthyl or cycloalkyl groups being unsubstituted or substituted by one or two R¹⁶ groups;

R³ represents a hydrogen atom or a $C_{1-6}$ alkyl group;

R⁴ represents a hydrogen atom or a $C_{1-6}$ alkyl group;

R⁵ represents a straight or branched $C_{1-6}$ alkyl, or $C_{2-6}$ alkenyl group uninterrupted or interrupted by one or more —O— or —S— atoms or —N(R⁷)— groups, and unsubstituted or substituted by a phenyl$C_{1-6}$alkyl, a phenyl$_{1-6}$alkoxy, phenyl, $C_{3-8}$heteroaryl, benzoloxyphenyl, —OH, —SH, $C_{1-6}$alkylthio, carboxy (—CO₂H), amino (—NH₂), carboxamido (—CONH₂) or guanidino —NHC(NH₂)=NH group, each of said phenyl, benzyl or heteroaryl groups being unsubstituted or substituted by a R¹⁰ substituent defined below, where R⁷ is a hydrogen atom or a $C_{1-6}$alkyl group; or R⁵ is a group —(Alk)$_n$R⁶ where Alk is an alkyl or alkenyl group uninterrupted or interrupted by one or more —O— or —S— atoms or —N(R⁷)— groups, n is 0 or 1, and R⁶ is a $C_{3-8}$cycloalkyl or $C_{3-8}$ cycloalkenyl group unsubstituted or substituted by one or two $C_{1-6}$alkyl, $C_{1-6}$ alkoxy, $C_{1-6}$alkylthio or hydroxyl groups;

X represents a group —NR¹⁰R¹¹ where R¹⁰ is a hydrogen atom or a $C_{1-6}$alkyl, $C_{2-4}$alkanoyl, phenyl$C_{1-3}$alkyl, phenyl, benzoyl, or phenyl$C_{1-3}$alkanoyl group and R¹¹ is a group —Alk¹N(R⁷)SO₂NR¹²R¹³—, where Alk¹ is a $C_{1-6}$alkyl, uninterrupted or interrupted by one or more —O— or —S— atoms or —N(R⁷)— or aminocarbonyloxy groups, and R¹² and R¹³, which are the same or different, is each a hydrogen atom or a straight or branched $C_{1-6}$ alkyl group, uninterrupted or interrupted by one or more —O— or —S— atoms or —N(R⁷)— or aminocarbonyloxy groups, and unsubstituted or substituted by a hydroxyl (—OH), carboxyl (—CO₂H), —CO₂R¹⁸, carboxamido (—CONH₂), —CONR¹²R¹³, amino (—NH₂), or —NR¹²R¹³ group, or R¹² and R¹³ are each a phenyl group, unsubstituted or substituted by one or two R⁶ substituents; or R¹² and R¹³, taken together with the nitrogen atom to which they are attached, form a morpholinyl, imidazolyl, piperazinyl, pyrrolyl, oxazolyl, thiazolyl, pyrazoyl, pyrrolidinyl, pyridinyl or pyrimidinyl group;

or a salt, solvate or hydrate thereof.

2. A compound according to claim 1 wherein R represents a —CONHOH group.

3. A compound according to claim 1 wherein R¹, R³ and R⁴ is each a hydrogen atom.

4. A compound according to claim 1 where R² is an unsubstituted or substituted phenylpropyl group.

5. A compound according to any of claim 1 wherein R⁵ is a cyclohexyl $C_{1-6}$ alkyl group.

6. A compound according to any of claim 1 wherein R⁵ is a cyclohexylmethyl group.

7. A compound according to claim 1 wherein Alk¹ is a $C_{1-3}$ alkyl group.

8. A compound of formula (1a)

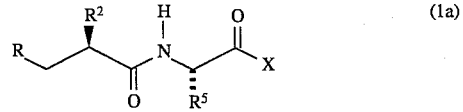

wherein R represents —CONHOH, carboxyl (—CO₂H) or —CO₂R¹⁸, where R¹⁸ is a straight or branched $C_{1-8}$ alkyl, benzyl, phenylethyl, phenylpropyl, 1-naphthylmethyl, 2-naphthylmethyl, phenyl, 1-naphthyl, 2-naphthyl phenyloxymethyl, phenyloxyethyl, 1-naphthyloxymethyl, 2-naphthyloxymethyl, $C_{1-8}$alkanoyloxy$C_{1-8}$alkyl, benzoyloxyethyl or benzoyloxypropyl group, each unsubstituted or substituted by one or more halogen atoms or $C_{1-4}$alkyl or $C_{1-4}$alkoxy groups;

R² represents a straight or branched $C_{1-6}$alkyl or $C_{2-6}$alkenyl group, unsubstituted or substituted by one or more $C_{1-6}$alkylthio, phenyl$C_{1-6}$alkoxy, phenyl$C_{3-6}$alkylthio, amino (—NH₂), carboxyl (—CO₂H) or —CO₂R¹⁸ groups; or R² is a phenyl, 1- or 2-naphthyl, phenyl$C_{1-6}$alkyl, 1- or 2-naphthyl$C_{1-6}$alkyl, $C_{3-8}$cycloalkyl, $C_{3-8}$cycloalkyl$C_{1-6}$alkyl, phenyl$C_{1-6}$alkoxy or phenylC$_{1-6}$alkythio group, each of said phenyl, naphthyl or cycloalkyl groups being unsubstituted or substituted by one or two R$^{16}$ groups;

R$^5$ represents a straight or branched C$_{1-6}$alkyl, or C$_{2-6}$alkenyl group uninterrupted or interrupted by one or more —O— or —S— atoms or —N(R$^7$)— groups, and unsubstituted or substituted by a phenylC$_{1-6}$alkyl, phenylC$_{1-6}$alkoxy, phenyl, C$_{3-8}$heteroaryl, benzyloxyphenyl, —OH, —SH, C$_{1-6}$alkylthio, carboxy (—CO$_2$H), amino (—NH$_2$), carboxamido (—CONH$_2$) or guanidino —NHC(NH$_2$)=NH group each of said phenyl, benzyl or heteroaryl groups being unsubstituted or substituted by a R$^{10}$ substituent defined below, where R$^7$ is a hydrogen atom or a C$_{1-6}$alkyl group; or R$^5$ is a group —(Alk)$_n$R$^6$ where Alk is an alkyl or alkenyl group uninterrupted or interrupted by one or more —O— or —S— atoms or —N(R$^7$)— groups, n is zero or an integer 1, and R$^6$ is a C$_{3-8}$cycloalkenyl group unsubstituted or substituted by one or two C$_{1-6}$alkyl, C$_{1-6}$alkoxy, C$_{1-6}$alkylthio or hydroxyl groups;

X represents a group —NR$^{10}$R$^{11}$ where R$^{10}$ is a hydrogen atom or a C$_{1-6}$alkyl, C$_{2-4}$alkanoyl, phenylC$_{1-3}$alkyl phenyl, benzoyl, or phenylC$_{1-3}$alkanoyl group, and R$^{11}$ is a group —Alk$^1$N(R$^7$)SO$_2$NR$^{12}$R$^{13}$, where Alk$^1$ is a C$_{1-6}$alkyl group, uninterrupted or interrupted by one or more —O— or —S— atoms or —N(R$^7$)— or aminocarbonyloxy groups, and R$^{12}$ and R$^{13}$, which are the same or different, is each a hydrogen atom or a straight or branched C$_{1-6}$alkyl group, uninterrupted or interrupted by one or more —O— or —S— atoms or —N(R$^7$)— or amino-carbonyloxy groups, and unsubstituted or substituted by a hydroxyl (—OH), carboxyl (—CO$_2$H), —CO$_2$R$^{18}$, carboxamido (—CONH$_2$), —CONR$^{12}$R$^{13}$, amino (—NH$_2$), or —NR$^{12}$R$^{13}$, or R$^{12}$ and R$^{13}$ when taken together with the nitrogen atom to which they are attached, form a morpholinyl, imidazolyl, piperazinyl, pyrrolyl, oxazolyl, thiazolyl, pyrazolyl, pyrrolidinyl, pyridinyl or pyrimidinyl group; or a salt, solvate, or hydrate thereof.

9. {4-Hydroxy-2-(R)-[3-(4-methylphenyl)propyl]succinyl}-L-β-cyclohexylalanine-N-[(2-morpholinesulphonylamino)ethyl]amide;

{4-(N-Hydroxyamino)-2-(R)-[3-(4-methylphenyl)propyl]succinyl}-L-β-cyclohexylalanine-N-[(2-morpholinesulphonylamino)ethyl]amide;

{4-(N-Hydroxyamino-2-(R)-[3-(4-chlorophenyl)propyl]succinyl}-L-β-cyclohexylalanine-N-[(2-morpholinesulphonylamino)ethyl]amide;

{4-N-Hydroxyamino-2-(R)-[3-(4-methylphenyl)propyl]succinyl}-L-β-cyclohexylalanine-N-[(2-dimethylsulphonylamino)propyl]amide;

or a salt, solvate, or hydrate thereof.

10. A pharmaceutical composition comprising a compound according to any one of claim 1 and a pharmaceutically acceptable diluent, carrier or excipient.

* * * * *